(12) United States Patent
Chen

(10) Patent No.: US 8,419,805 B2
(45) Date of Patent: Apr. 16, 2013

(54) SILICONE LINER UNIT USED FOR PROSTHETIC LIMBS

(76) Inventor: Hui-Mei Chen, Shu Lin (TW)

( * ) Notice: Subject to any disclaimer, the term of this patent is extended or adjusted under 35 U.S.C. 154(b) by 32 days.

(21) Appl. No.: 12/946,810

(22) Filed: Nov. 15, 2010

(65) Prior Publication Data

US 2012/0123560 A1    May 17, 2012

(51) Int. Cl.
*A61F 2/80*    (2006.01)

(52) U.S. Cl.
USPC ............................................................ 623/36

(58) Field of Classification Search ............... 623/32–37
See application file for complete search history.

(56) References Cited

U.S. PATENT DOCUMENTS

2009/0240344 A1 *    9/2009    Colvin et al. ................... 623/36

* cited by examiner

*Primary Examiner* — Bruce E Snow
(74) *Attorney, Agent, or Firm* — Chun-Ming Shih

(57) ABSTRACT

A silicone liner unit used for prosthetic limbs includes a silicone liner portion, a smooth outer layer, an inner layer and an innermost layer. The silicone liner portion is made of silicone elastomer liner and has an open end. The smooth outer layer is made of Hl a-methyl-Disilane or a compound containing poly-p-xylene and may have a slightly protrusive pattern on its outer surface. The inner layer is made of fibrous tissue and is flexible. The innermost layer is disposed on top of the inner layer and is made of silicone elastomer liner to enhance the strength of the improved silicone liner unit. The smooth outer layer allows the improved silicone liner unit to be put on and taken off easily.

3 Claims, 5 Drawing Sheets

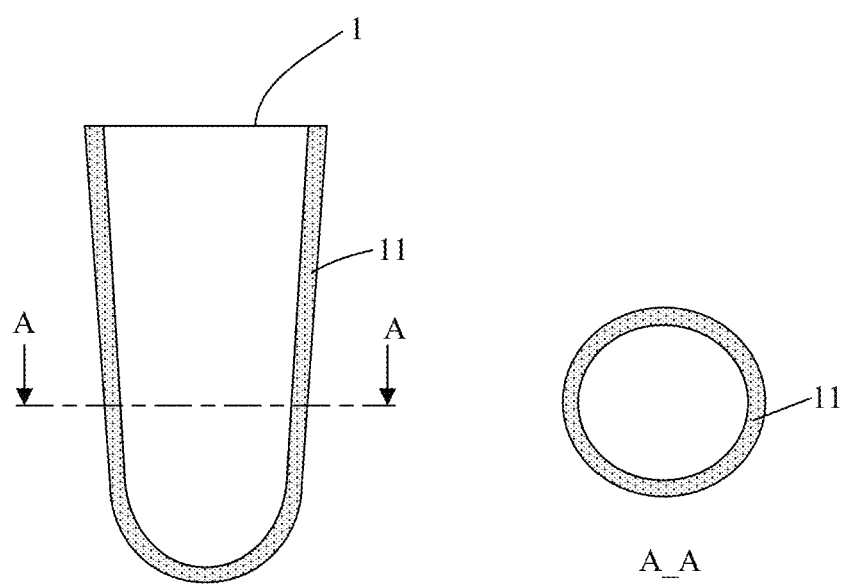
Prior Art
Fig. 1A
Prior Art
Fig. 1B

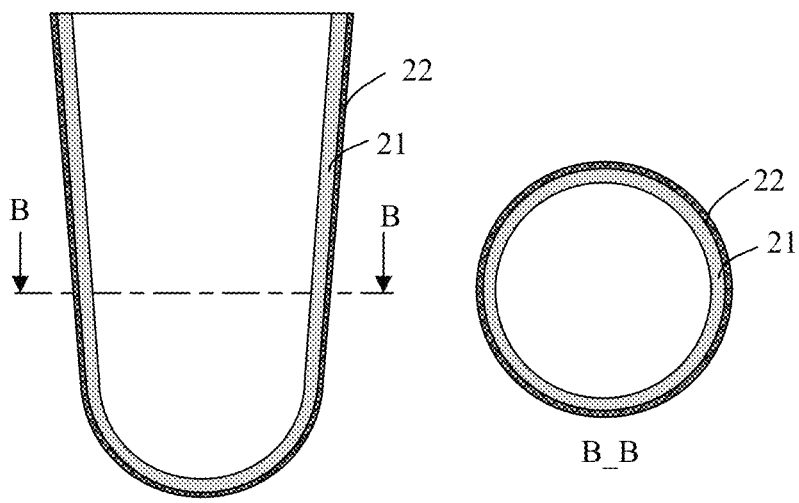
*Fig. 2A*    *Fig. 2B*

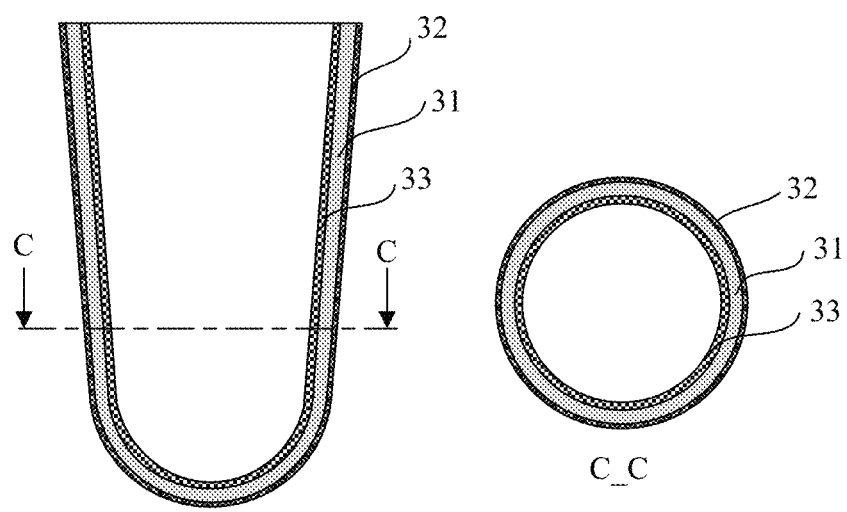
Fig. 3A　　Fig. 3B

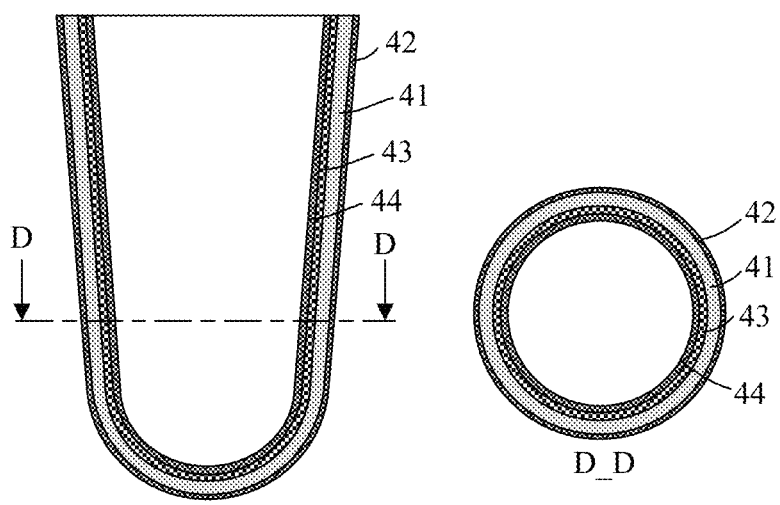
Fig. 4A          Fig. 4B

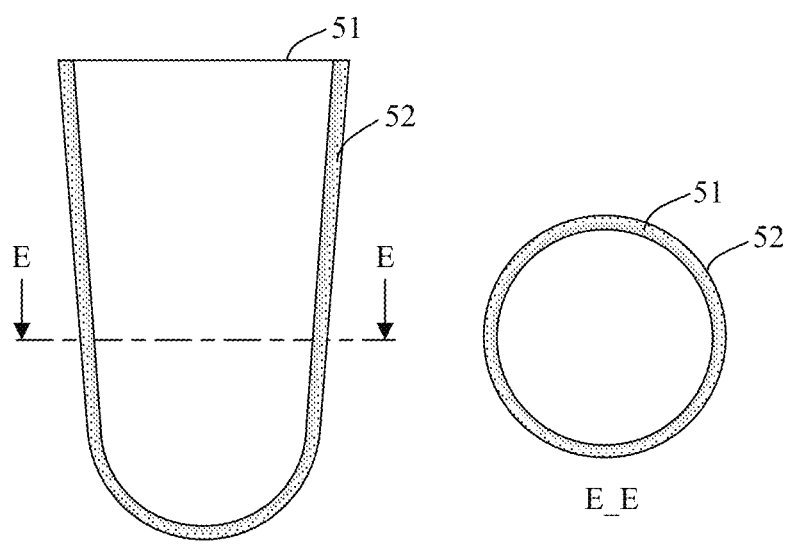
Fig. 5A  Fig. 5B

SILICONE LINER UNIT USED FOR PROSTHETIC LIMBS

BACKGROUND OF THE INVENTION

1. Field of the invention

The invention generally relates to an improved silicone liner unit used for prosthetic limbs. More particularly, the invention relates to an improved silicone liner unit that is comfortable to wear and may be put on and taken off easily.

2. Description of the related art

People with an amputated limb often wear a prosthetic limb. A silicone liner unit is usually worn before they put on a prosthetic limb to protect their amputated limb. The silicone liner unit of the prior art does protect the amputated limb and can enhance comfort. However, it is not easy to put on and take off because it is made of silicone elastomer liner and hence has a higher level of friction.

FIG. 1A is a sectional view showing the conventional silicone liner unit. FIG. 1B is a cross-sectional view along the line A-A of FIG. 1A. The conventional silicone liner unit 1 is made of a layer 11 that is made of silicone elastomer liner and hence is flexible. Therefore, the conventional silicone liner unit 1 is comfortable to wear. However, the layer 11 may be damaged after the silicone liner unit 1 is used for a long period of time.

To improve the conventional silicone liner unit, its strengthen and flexibility need to be enhanced. In addition, its inner surface should be able to hinder the growth of bacteria. Also, its friction should be reduced so that it can be put on and take off easily.

From the above, we can see that the conventional silicone liner unit has many disadvantages and need to be improved. To eliminate the disadvantages in the prior art, the inventor has put a lot of effort into the subject and has successfully come up with the improved silicone liner unit of the present invention.

SUMMARY OF THE INVENTION

An object of the present invention is to provide an improved silicone liner unit that has a high level of strength, a lower level of friction on its surface and a smooth outer layer that can hinder the growth of bacteria and is easy to put on and take off.

Another object of the present invention is to provide an improved silicone liner unit that may be put on and taken off more comfortably.

A third object of the present invention is to provide an improved silicone liner unit that is flexible.

To reach these objects, the improved silicone liner unit of the present invention is disclosed. The improved silicone liner unit of the present invention comprises a silicone liner portion, a smooth outer layer, an inner layer and an innermost layer. The silicone liner portion is made of silicone elastomer liner and has an open end. The smooth layer is made of Hl a-methyl-Disilane or a compound containing poly-p-xylene and may have a slightly protrusive pattern on its outer surface. The inner layer is made of fibrous tissue and is flexible. The innermost layer is made of silicone elastomer liner and is disposed on the inner layer. The smooth layer is made by vacuum chemical vapor deposition or plasma enhanced chemical vapor deposition. The smooth outer layer is made by sand blasting or a mold with a slightly protrusive pattern. Sand blasting may be done on the outer surface of the improved silicone liner unit or the surface of the mold. The Hl a-methyl-Disilane is hexamethyl disilane and the compound containing poly-p-xylene is parylene. The improved silicone liner unit further comprises a connective piece that is disposed on the closed end of the silicone liner portion to connect the silicone liner portion with a prosthetic limb.

In comparison to the prior art, the improved silicone liner unit of the present invention has the following advantages:

1. The silicone liner unit of the prior art is made of silicone elastomer liner and hence has a high level of friction. Therefore, it is difficult to put on and take off. The outer surface of the improved silicone liner unit of the present invention has a lower level of friction, can hinder the growth of bacteria and allows it to be put on and taken off easily.

2. The silicone liner portion has an inner layer that is made of fibrous tissue and is flexible. In addition, the silicone liner portion has an innermost layer. The innermost layer is made of silicone elastomer liner and is disposed on the inner layer. These two layers can enhance the strength of the improved silicone liner unit of the present invention.

BRIEF DESCRIPTION OF THE DRAWINGS

The drawings disclose several illustrative embodiments of the present invention which serve to exemplify the various advantages and objects hereof, and are as follows:

FIG. 1A is a sectional view showing the conventional silicone liner unit of the prior art.

FIG. 1B is a cross-sectional view along the line A-A of FIG. 1A.

FIG. 2A is a sectional view of the first embodiment of the present invention.

FIG. 2B is a cross-sectional view along the line B-B of FIG. 2A.

FIG. 3A is a sectional view of the second embodiment of the present invention.

FIG. 3B is a cross-sectional view along the line C-C of FIG. 3A.

FIG. 4A is a sectional view of the third embodiment of the present invention.

FIG. 4B is a cross-sectional view along the line D-D of FIG. 4A.

FIG. 5A is a sectional view of the fourth embodiment of the present invention.

FIG. 5B is a cross-sectional view along the line E-E of FIG. 5A.

DETAILED DESCRIPTION OF THE PREFERRED EMBODIMENTS

Please see FIGS. 2A to 2B. FIG. 2A is a sectional view of the first embodiment of the present invention. FIG. 2B is a cross-sectional view along the line B-B of FIG. 2A. In the first embodiment, the improved silicone liner unit of the present invention comprises a silicone liner portion 21 and a smooth outer layer 22. The silicone liner portion 21 is made of silicone elastomer liner and has an open end. The smooth outer layer 22 is made of Hl a-methyl-Disilane or a compound containing poly-p-xylene.

Please see FIGS. 3A to 3B. FIG. 3A is a sectional view of the second embodiment of the present invention. FIG. 3B is a cross-sectional view along the line C-C of FIG. 3A. In the second embodiment, the improved silicone liner unit of the present invention comprises a silicone liner portion 31, a smooth outer layer 32 and an inner layer 33. The silicone liner portion 31 is made of silicone elastomer liner and has an open end. The smooth outer layer 32 is made of Hl a-methyl- Disilane or a compound containing poly-p-xylene. The inner layer 33 is made of fibrous tissue and is flexible.

Please see FIGS. 4A to 4B. FIG. 4A is a sectional view of the third embodiment of the present invention. FIG. 4B is a cross-sectional view along the line D-D of FIG. 4A. In the third embodiment, the improved silicone liner unit of the present invention comprises a silicone liner portion 41, a smooth outer layer 42, an inner layer 43 and an innermost layer 44. The silicone liner portion 41 is made of silicone elastomer liner and has an open end. The smooth outer layer 42 is made of Hl a-methyl-Disilane or a compound containing poly-p-xylene. The inner layer 43 is made of fibrous tissue and is flexible. The innermost layer 44 is made of silicone elastomer liner.

Please see FIGS. 5A to 5B. FIG. 5A is a sectional view of the fourth embodiment of the present invention. FIG. 5B is a cross-sectional view along the line E-E of FIG. 5A. In the fourth embodiment, the improved silicone liner unit of the present invention comprises a silicone liner portion 51, a smooth outer layer 52, an inner layer 53 and an innermost layer 54. The silicone liner portion 51 is made of silicone elastomer liner and has an open end. The smooth outer layer 52 may have a slightly protrusive pattern on its outer surface. The inner layer 53 is made of fibrous tissue and is flexible. The innermost layer 54 is made of silicone elastomer liner.

The smooth outer layer in the first, second and third embodiments is made by vacuum chemical vapor deposition or plasma enhanced chemical vapor deposition. The smooth outer layer in the fourth embodiment is made by sand blasting or a mold with a slightly protrusive pattern. Sand blasting may be done on the outer surface of the improved silicone liner unit or the surface of the mold. The layers 22, 32, 42 and 44 are made of Hl a-methyl-Disilane which is hexamethyl disilane, or a compound containing poly-p-xylene which is parylene A connective piece is disposed on the closed end of the silicone liner portion 21, 31, 41 and 51 to connect the silicone liner portion with a prosthetic limb.

What is claimed is:

1. A silicone liner unit used for prosthetic limbs, comprising:
   a silicone liner portion, which is made of silicone elastomer layer and has an open end;
   a smooth outer layer capable of hindering growth of bacteria, which is formed on an outside surface of the silicone liner portion;
   an inner layer, which is made of fibrous tissue and is flexible, formed on an inner surface of the silicone liner portion to enhance strength of the silicone liner unit; and
   an innermost layer, which is made of a silicone elastomer layer, formed on an inner surface of the inner layer,
   wherein the smooth outer layer is made of Hl a-methyl-Disilane, and the Hl a-methyl-Disilane is hexamethyl disilane.

2. The silicone liner unit as in claim 1, wherein the smooth outer layer is made by vacuum chemical vapor deposition or plasma enhanced chemical vapor deposition.

3. The silicone liner unit as in claim 1, further comprising a connective piece that is disposed on an closed end of the silicone liner portion to connect the silicone liner portion with a prosthetic limb.

* * * * *